(12) United States Patent
Inoue et al.

(10) Patent No.: US 9,856,210 B2
(45) Date of Patent: Jan. 2, 2018

(54) PHARMACEUTICAL COMPOSITION FOR PREVENTION AND TREATMENT OF AMYOTROPHIC LATERAL SCLEROSIS

(75) Inventors: Haruhisa Inoue, Kyoto (JP); Shiho Kitaoka, Kyoto (JP); Kayoko Tsukita, Kyoto (JP); Ryosuke Takahashi, Kyoto (JP); Gaku Murakami, Kyoto (JP); Norio Nakatsuji, Kyoto (JP); Motonari Uesugi, Kyoto (JP); Yasuyuki Asai; Ayako Asai, legal representative, Tokyo (JP); Yuji Amagai, Kyoto (JP); Kazuhiro Aiba, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 13/820,420

(22) PCT Filed: Sep. 2, 2011

(86) PCT No.: PCT/JP2011/070538
§ 371 (c)(1),
(2), (4) Date: May 6, 2013

(87) PCT Pub. No.: WO2012/029994
PCT Pub. Date: Mar. 8, 2012

(65) Prior Publication Data
US 2013/0225642 A1  Aug. 29, 2013

Related U.S. Application Data

(60) Provisional application No. 61/379,558, filed on Sep. 2, 2010.

(51) Int. Cl.
*A61K 31/17* (2006.01)
*A61K 31/44* (2006.01)
*A61K 45/06* (2006.01)
*C07C 275/30* (2006.01)

(52) U.S. Cl.
CPC ............ *C07C 275/30* (2013.01); *A61K 31/17* (2013.01); *A61K 31/44* (2013.01); *A61K 45/06* (2013.01)

(58) Field of Classification Search
None
See application file for complete search history.

(56) References Cited

U.S. PATENT DOCUMENTS

| 2003/0144278 A1 | 7/2003 | Riedl et al. | |
|---|---|---|---|
| 2007/0105142 A1* | 5/2007 | Wilhelm | C12Q 1/6886 435/6.14 |
| 2009/0004213 A1* | 1/2009 | Singh | A61K 39/0011 424/185.1 |
| 2009/0023736 A1* | 1/2009 | Koya | A61K 45/06 514/238.2 |
| 2009/0053168 A1* | 2/2009 | Rickles | A61K 45/06 424/85.2 |
| 2009/0098137 A1* | 4/2009 | Burke | A61K 31/132 424/141.1 |
| 2009/0105285 A1* | 4/2009 | Lane | A61K 31/00 514/266.21 |
| 2009/0170914 A1* | 7/2009 | Bornancin | C07D 277/82 514/367 |
| 2011/0015272 A1 | 1/2011 | Snow et al. | |

FOREIGN PATENT DOCUMENTS

| WO | WO 00/41698 A1 | 7/2000 | |
|---|---|---|---|
| WO | WO 03/093250 A2 | 11/2003 | |
| WO | WO 2005/092843 A1 | 10/2005 | |
| WO | WO 2006/020145 A2 | 2/2006 | |
| WO | WO 2008/031835 A2 | 3/2008 | |
| WO | WO 2008/115263 A2 | 9/2008 | |
| WO | WO/2008/133884 | * 11/2008 | ........... A61K 31/551 |
| WO | WO 2010/019911 A2 | 2/2010 | |

OTHER PUBLICATIONS

Carlesi et al. 2011 "strategies for clinical approach to neurodegeneration in amyotrophic lateral sclerosis" Arch Itali de Biologie 149:151-167.*
Bendotti and Carri 2004 "lessons from models of sod1-linked familial als" trends mol med 10(8):393-400.*
Andersen 2004 "Oxidative stress in neurodegeneration: cause or consequence?" Nature reviews Neuroscience 5:S18-S25 (abstract only).*
Bendotti and Carri 2004 "Lessons from models of SOD1-linked familial ALS" Trends in Molecular Medicine 10(8):393-400.*
Furukawa and O'Halloran "Posttranslational Modifications in Cu,Zn-Superoxide Dismutase and Mutations Associated with amyotrophic lateral sclerosis" Antioxid Redox Signal 8(5-6):847-867.*
Roy et al. 1998 "Glutamate potentiates the toxicity of mutant Cu/Zn-superoxide dismutase in motor neurons by postsynaptic calcium-dependent mechanisms" J Neurosci 18(23):9673-9684.*
Cudkowicz 2006 "trial of celecoxib in amyotrophic lateral sclerosis" Ann Neurol 60:22-31.*
Kalra 2003 "gabapentin therapy for amyotrophic lateral sclerosis: lack of improvement in neuronal integrity shown by MR spectroscopy" AJNR Am J Neuronadiol 24:476-480.*
Meissner 2010 "mutant superoxide dismutase 1-induced IL-1.beta. accelarates ALS pathogenesis" PNAS 107(29):13046-13050.*
Gurney 1996 "benefit of vitamin E, rizuzole, and gabapentin in a transgenic model of familial amyotrophic lateral sclerosis" Ann neurol 39(2):147-57 (abstract only).*
Isaacs 2008 "Lack of TAR-DNA binding protein-43 (TDP-43) pathology in human prion diseases" Neuropathology App Neurobiol 34: 446-456.*
Romano 1996 "reduction of fasciculations in patients with amyotrophic lateral sclerosis with the use of gabapentin" Arch Neurol 53: 716.*

(Continued)

Primary Examiner — Adam Weidner
(74) Attorney, Agent, or Firm — Leydig, Voit & Mayer, Ltd.

(57) ABSTRACT

The present invention provides a prophylactic or therapeutic agent for amyotrophic lateral sclerosis, containing a 1,3-diphenylurea derivative or multikinase inhibitor.

6 Claims, 4 Drawing Sheets

(56) References Cited

OTHER PUBLICATIONS

NCI dictionary 2017 "sorafenib tosylate" accessed from cancer.gov on Jan. 5, 2017.*
SCBT 2017 "Sorafenib (CAS 284461-73-0)" accessed from scbt.com on Jan. 5, 2017.*
Wikipedia 2017 "Sorafenib" accessed from wikipedia.org on Jan. 5, 2017.*
Bruijn et al., *Annu. Rev. Neurosci.*, 27: 723-749 (2004).
Burdo et al., *Brain Res.*, 1189: 12-22 (2008).
Burgess et al., *CNS & Neurological Disorders—Drug Targets*, 9(1): 120-127 (2010).
Gollob et al., *Seminars in Oncology*, 33: 392-406 (2006).
Japanese Patent Office, International Search Report in International Patent Application No. PCT/JP2011/070538 (dated Oct. 11, 2011).
International Bureau of WIPO, International Preliminary Report on Patentability in International Patent Application No. PCT/JP2011/070538 (dated Mar. 5, 2013).
European Patent Office, Extended European Search Report in European Patent Application No. 11822002.9 (dated Jan. 15, 2014).
Gordon, "Amyotrophic Lateral Sclerosis: an update for 2013 Clinical Features, Pathophysiology, Management and Therapeutic Trials," *Aging and Disease*, 4(5): 295-310 (Oct. 2013).
U.S. National Library of Medicine (NLM), "Amyotrophic lateral sclerosis" in *Genetics Home Reference* [retrieved from http://ghr.nlm.nih.gov/condition/amyotrophic-lateral-sclerosis/show/print] (reviewed Aug. 2012 and published Dec. 16, 2014).
Vaccaro et al., "Methylene Blue Protects against TDP-43 and FUS Neuronal Toxicity in *C. elegans* and *D. rerio*," *PLoS One*, 7(7): e42117 [doi:10.1371/journal.pone.0042117] (Jul. 27, 2012).
MacKenzie et al., "Pathological TDP-43 Distinguishes Sporadic Amyotrophic Lateral Sclerosis from Amyotrophic Lateral Sclerosis with SOD1 Mutations," *American Neurological Association*, 61(5):427-434 (2007).
Pagani et al., "Autoimmunity in Amyotrophic Lateral Sclerosis: Past and Present," *Neurology Research International*, 2011: Article ID 497080 (2011).
Silani et al., "Plasma Exchange Ineffective in Amyotrophic Lateral Sclerosis," *Arch. Neurol.*, 37: 511-513 (1980).

* cited by examiner

PHARMACEUTICAL COMPOSITION FOR PREVENTION AND TREATMENT OF AMYOTROPHIC LATERAL SCLEROSIS

CROSS-REFERENCE TO RELATED APPLICATIONS

This patent application is the U.S. national phase of International Patent Application PCT/JP2011/070538, filed on Sep. 2, 2011, which claims the benefit of U.S. Provisional Patent Application No. 61/379,558, filed Sep. 2, 2010, which are incorporated by reference in their entireties herein.

TECHNICAL FIELD OF THE INVENTION

The present invention relates to a pharmaceutical composition for the prevention or treatment of amyotrophic lateral sclerosis. More particularly, the present invention relates to a pharmaceutical composition for the prevention or treatment of amyotrophic lateral sclerosis, comprising a 1,3-diphenylurea derivative or multikinase inhibitor.

BACKGROUND OF THE INVENTION

Amyotrophic lateral sclerosis (hereinafter, ALS) is a motor neuron disease of poor prognosis, which develops at middle ages and thereafter and causes progressive paralysis of skeletal muscles. It is designated as a disease in the project for investigation and research into specific diseases sponsored by the Ministry of Health, Labor and Welfare of Japan. More than about 90% of cases of ALS are sporadic and the cause is unknown, whereas the remaining 10% are familial cases. To explain the causal factor in the latter cases, the gain-of-toxic function theory is likely wherein motor neuron death is caused by the cytotoxicity newly gained by mutated SOD1 (Cu/Zn superoxide dismutase) as a result of a point mutation of the SOD1 gene (1).

The only currently commercially available therapeutic drug for ALS is riluzole (Rilutek™, Aventis), a glutamate receptor antagonist possessing glutamate suppressing action (2).

In recent years, Yamanaka et al. succeeded in establishing iPS cells by transferring four genes into human skin fibroblasts (3, 4). Similarly, Thomson and his colleagues produced human iPS cells using Nanog and Lin28 in place of Klf4 and c-Myc (5, 6). Because the iPS cells thus obtained can be differentiated into cells of various tissues after being generated using cells derived from the patient to be treated, they are thought to enable reproduction of the pathologic condition in vitro. In fact, the above-described method was successfully applied to generate iPS cells from ALS patient and differentiate into neurons (7). Thus, using neurons induced from iPS cells derived from ALS patients, screening for a contributory therapeutic drug has been ongoing.

According to the IUPAC nomenclature system, sorafenib is a 1,3-diphenylurea derivative compound shown by 4-(4-{3-[4-chloro-3-(trifluoromethyl)phenyl]ureido}phenoxy)-N2-methylpyrimidine-2-carboxyamide.4-methylbenzene-sulfonic acid (8), which is known as a multikinase inhibitor that inhibits kinases such as Raf1, blood vessel endothelial growth factor receptor (VEGFR)-2, -3, Flt3, platelet-derived growth factor receptor (PDGFR)-b, c-kit and the like, and is used as a therapeutic drug for progressive renal cell cancer (9). However, its effect on ALS is not known at all.

CITED DOCUMENTS

1. Bruijn, L. I. et al., *Annu. Rev. Neurosci.*, 27: 723-749 (2004)
2. AU 666150 B2
3. WO 2007/069666 A1
4. Takahashi, K. et al., *Cell*, 131: 861-872 (2007)
5. WO 2008/118820 A2
6. Yu, J. et al., *Science*, 318: 917-1920 (2007)
7. Dimos, J. T. et al., *Science*, 321: 1218-21 (2008)
8. WO 2000/041698
9. Gollob, J. A. et al., *Semin. Oncol.*, 33: 392-406 (2006)

SUMMARY OF THE INVENTION

It is an object of the present invention to provide a pharmaceutical composition for the prevention or treatment of ALS. Accordingly, the problem to be solved by the present invention is to produce a pharmaceutical composition useful for the prevention or treatment of ALS.

To solve this problem, the present inventors have established iPS cells from fibroblasts of an ALS patient, and differentiated them into astrocytes. Here, with a focus on the amount of SOD1 expressed, the astrocytes thus obtained and a test compound were brought into contact with each other, and a compound that reduces the amount expressed was screened for. As a result, a 1,3-diphenylurea derivative was confirmed to reduce the amount of SOD1 expressed. Then, sorafenib, which is a multikinase inhibitor, was used as the 1,3-diphenylurea derivative. As a result, sorafenib was also confirmed to reduce the amount of SOD1 expressed.

Judging from the above results, the present inventors have found that a 1,3-diphenylurea derivative or multikinase is inhibitor is useful for the prevention or treatment of ALS, which resulted in the completion of the present invention.

Accordingly, the present invention provides the following:

[1] An agent for the prevention or treatment of amyotrophic lateral sclerosis, comprising a 1,3-diphenylurea derivative represented by the formula (1):

wherein
$R_1$ and $R_2$ are each independently a hydrogen atom, a halogen atom, a hydroxy group, an amino group, a trifluoromethyl group, a C1-C4 alkyl group or a C1-C4 alkoxy group; and
$R_3$ and $R_4$ are each independently a hydrogen atom, a halogen atom, a hydroxy group, an amino group, a carboxyl group, a C1-C4 alkoxy group, a C1-C4 alkoxy-carbonyl group, a 5- or 6-membered heteroaryloxy group, a carboxy-substituted 5- or 6-membered heteroaryloxy group, a C1-C4 alkoxy-carbonyl-substituted 5- or 6-membered heteroaryloxy group, a carbamoyl-substituted 5- or 6-membered heteroaryloxy group, a C1-C4 alkyl-carbamoyl-substituted 5- or 6-membered heteroaryloxy group, an aryloxy group, a carboxy-substituted aryloxy group, a C1-C4 alkyl-carbonyl-substituted aryloxy group, a carbamoyl-substituted aryloxy group, or a C1-C4 alkyl-carbamoyl-substituted aryloxy group,
or a pharmaceutically acceptable salt thereof.

[2] The agent according to [1], wherein $R_1$ and $R_2$ are each independently a hydrogen atom, a halogen atom or a trifluoromethyl group, and $R_3$ and $R_4$ are each independently a hydrogen atom, a halogen atom, or a C1-C4 alkyl-carbamoyl-substituted 5- or 6-membered heteroaryloxy group.

[3] The agent according to [1], wherein the 1,3-diphenylurea derivative is a compound represented by the formula (2):

[4] The agent according to [1], wherein the 1,3-diphenylurea derivative is a compound represented by the formula (3):

[5] The agent according to [1], wherein the 1,3-diphenylurea derivative is a compound represented by the formula (4):

[6] A method for the prevention or treatment of amyotrophic lateral sclerosis in a mammal, comprising administering to the mammal an effective amount of a 1,3-diphenylurea derivative represented by the formula (1):

wherein $R_1$ and $R_2$ are each independently a hydrogen atom, a halogen atom, a hydroxy group, an amino group, a trifluoromethyl group, a C1-C4 alkyl group or a C1-C4 alkoxy group; and $R_3$ and $R_4$ are each independently a hydrogen atom, a halogen atom, a hydroxy group, an amino group, a carboxyl group, a C1-C4 alkoxy group, a C1-C4 alkoxy-carbonyl group, a 5- or 6-membered heteroaryloxy group, a carboxy-substituted 5- or 6-membered heteroaryloxy group, a C1-C4 alkoxy-carbonyl-substituted 5- or 6-membered heteroaryloxy group, a carbamoyl-substituted 5- or 6-membered heteroaryloxy group, a C1-C4 alkyl-carbamoyl-substituted 5- or 6-membered heteroaryloxy group, an aryloxy group, a carboxy-substituted aryloxy group, a C1-C4 alkyl-carbonyl-substituted aryloxy group, a carbamoyl-substituted aryloxy group, or a C1-C4 alkyl-carbamoyl-substituted aryloxy group, or a pharmaceutically acceptable salt thereof.

[7] An agent for the prevention or treatment of amyotrophic lateral sclerosis, comprising a multikinase inhibitor.

[8] The agent according to [7], wherein the multikinase inhibitor has a Raf1 inhibitory effect.

[9] The agent according to [7], wherein the multikinase inhibitor is sorafenib.

[10] A method for the prevention or treatment of amyotrophic lateral sclerosis in a mammal, comprising administering an effective amount of a multikinase inhibitor to the mammal.

[11] The agent according to [1] or [7], wherein the amyotrophic lateral sclerosis is familial amyotrophic lateral sclerosis.

[12] The agent according to [11], wherein the familial amyotrophic lateral sclerosis is accompanied by a mutation of the SOD1 gene.

[13] The agent according to [12], wherein the mutation of the SOD1 gene does not cause the SOD activity of the gene product to be lost.

According to the present invention, it is possible to use a 1,3-diphenylurea derivative or multikinase inhibitor to prevent or treat ALS, since they can reduce the amount of SOD1 gene expressed.

BRIEF DESCRIPTION OF THE DRAWINGS

FIG. 1 A shows the luciferase activity when urea and N-(3-fluorophenyl)-N'-[4-(trifluoromethyl)phenyl](UFTP) (0 μM, 1.25 μM, 2.5 μM, 5.0 μM, 10.0 μM, 20.0 μM, 40.0 μM or 80.0 μM) were added to human neuroglioma H4 cell possessing SOD1-secreted luciferase reporter. FIG. 1 B shows the results of ELISA measurement of SOD1 when UFTP (0 μM, 2.5 μM, 5.0 μM, 10.0 μM, 20.0 μM or 40.0 μM) was added to human neuroglioma H4 cell. FIG. 1 C shows the results of WST-1 assay when UFTP (0 μM, 10.0 μM, 20.0 μM or 40.0 μM) was added to human neuroglioma H4 cell.

FIG. 2 A shows the luciferase activity when urea and N-(3-chlorophenyl)-N'-[4-(trifluoromethyl)phenyl](UCTP) (0 μM, 1.25 μM, 2.5 μM, 5.0 μM, 10.0 μM, 20.0 μM, 40.0 μM or 80.0 μM) were added to human neuroglioma H4 cell possessing SOD1-secreted luciferase reporter. FIG. 2 B shows the results of ELISA measurement of SOD1 when UCTP (0 μM, 2.5 μM, 5.0 μM, 10.0 μM, 20.0 μM or 40.0 μM) was added to human neuroglioma H4 cell. FIG. 2 C shows the results of WST-1 assay when UCTP (0 μM, 10.0 μM, 20.0 μM or 40.0 μM) was added to human neuroglioma H4 cell.

FIG. 3 A shows the luciferase activity when sorafenib tosylate (0 μM, 1.25 μM, 2.5 μM, 5.0 μM, 10.0 μM, 20.0 μM, 40.0 μM or 80.0 μM) was added to human neuroglioma H4 cell possessing SOD1-secreted luciferase reporter. FIG. 3 B shows the results of ELISA measurement of SOD1 when sorafenib tosylate (0 μM, 2.5 μM, 5.0 μM, 10.0 μM, 20.0 μM or 40.0 μM) was added to human neuroglioma H4 cell. FIG. 3 C shows the results of WST-1 assay when sorafenib tosylate (0 μM, 1.25 μM, 2.5 μM, 5.0 μM, 10.0 μM, 20.0 μM, 40.0 μM or 80.0 μM) was added to human neuroglioma H4 cell. FIG. 3 D shows the results of the measurement by the western blotting of the amount of intracellular SOD1 expressed when vehicle alone (0.5% DMSO; veh), sorafenib tosylate (1.0 μM, 3.0 μM, 10.0 μM or 30.0 μM), or cycloheximide (CHX) (10 μg/ml) was added to astrocytes induced to differentiate from a human iPS cell. β-actin was used as the internal standard.

DETAILED DESCRIPTION OF THE INVENTION

The present invention provides a pharmaceutical composition comprising a 1,3-diphenylurea derivative or multikinase inhibitor for the prevention or treatment of amyotrophic lateral sclerosis (ALS).

In the present invention, it is desirable that the amyotrophic lateral sclerosis to be treated be familial amyotrophic lateral sclerosis. In a more preferred embodiment, the subject disease is familial amyotrophic lateral sclerosis having a mutation of SOD1, for example, cases wherein the mutation of the SOD1 gene does not cause the SOD activity of the gene product to be lost. As examples of mutations of the SOD1 gene that do not cause the SOD activity to be lost, mutations in the 4th exon in the mRNA of SOD1 (308-505 in the mRNA), specifically mutations wherein leucine at position 106 is converted, preferably mutations wherein the leucine is substituted by another amino acid, preferably by valine, can be mentioned.

The active ingredient of the agent for the prevention or treatment of ALS of the present invention is a 1,3-diphenylurea derivative represented by the formula (1)

(1)

wherein
$R_1$ and $R_2$ are each independently a hydrogen atom, a halogen atom, a hydroxy group, an amino group, a trifluoromethyl group, a C1-C4 alkyl group or a C1-C4 alkoxy group; and
$R_3$ and $R_4$ are each independently a hydrogen atom, a halogen atom, a hydroxy group, an amino group, a carboxyl group, a C1-C4 alkoxy group, a C1-C4 alkoxy-carbonyl group, a 5- or 6-membered heteroaryloxy group, a carboxy-substituted 5- or 6-membered heteroaryloxy group, a C1-C4 alkoxy-carbonyl-substituted 5- or 6-membered heteroaryloxy group, a carbamoyl-substituted 5- or 6-membered heteroaryloxy group, a C1-C4 alkyl-carbamoyl-substituted 5- or 6-membered heteroaryloxy group, an aryloxy group, a carboxy-substituted aryloxy group, a C1-C4 alkyl-carbonyl-substituted aryloxy group, a carbamoyl-substituted aryloxy group, or a C1-C4 alkyl-carbamoyl-substituted aryloxy group.

In the present specification, the halogen atom means a fluorine atom, a chlorine atom, a bromine atom or an iodine atom, with preference given to a fluorine atom or a chlorine atom.

In the present specification, the C1-C4 alkyl group means a linear or branched chain saturated hydrocarbon group having a carbon number of 1-4, namely, methyl, ethyl, propyl, isopropyl, n-butyl, sec-butyl, isobutyl or tert-butyl.

In the present specification, the C1-C4 alkoxy group means —O— to which a C1-C4 alkyl group is bonded, namely, methoxy, ethoxy, propoxy, isopropoxy, butoxy, sec-butoxy, isobutoxy or tert-butoxy.

In the present specification, the C1-C4 alkoxy-carbonyl group means —O— to which a C1-C4 alkoxy group is bonded, namely, methoxycarbonyl, ethoxycarbonyl, propoxycarbonyl, isopropoxycarbonyl, butoxycarbonyl, sec-butoxycarbonyl, isobutoxycarbonyl or tert-butoxycarbonyl.

In the present specification, the 5- or 6-membered heteroaryl group means a 5- or 6-membered aromatic group containing, as a ring-constituting atom besides carbon atom, 1 to 4 hetero atoms selected from an oxygen atom, a sulfur atom and a nitrogen atom (optionally oxidized). Specific preferable examples thereof include pyrrolyl, furyl, thienyl, imidazolyl, oxazolyl, thiazolyl, pyrazolyl, isoxazolyl, isothiazolyl, pyridyl, pyridazinyl, pyrimidinyl, pyrazinyl and the like.

In the present specification, the 5- or 6-membered heteroaryloxy group means —O— to which a 5- or 6-membered heteroaryl group is bonded. Specific preferable examples thereof include pyrrolyloxy, furyloxy, thienyloxy, imidazolyloxy, oxazolyloxy, thiazolyloxy, pyrazolyloxy, isooxazolyloxy, isothiazolyloxy, pyridyloxy, pyridazinyloxy, pyrimidinyloxy, pyrazinyloxy and the like.

In the present specification, the carboxy-substituted 5- or 6-membered heteroaryloxy group means a 5- or 6-membered heteroaryloxy group wherein a carboxy group is substituted at a substitutable position of the 5- or 6-membered heteroaryl ring. Specific preferable examples thereof include carboxypyrrolyloxy (e.g., 2-carboxy-4-pyrrolyloxy etc.), carboxyfuryloxy (e.g., 2-carboxy-4-furyloxy etc.), carboxythienyloxy (e.g., 2-carboxy-4-thienyloxy etc.), carboxyimidazolyloxy (e.g., 2-carboxy-4-imidazolyloxy etc.), carboxyoxazolyloxy (e.g., 2-carboxy-4-oxazolyloxy etc.), carboxythiazolyloxy (e.g., 2-carboxy-4-thiazolyloxy etc.), carboxypyrazolyloxy (e.g., 3-carboxy-5-pyrazolyloxy etc.), carboxyisooxazolyloxy (e.g., 3-carboxy-5-isooxazolyloxy etc.), carboxyisothiazolyloxy (e.g., 3-carboxy-5-isothiazolyloxy etc.), carboxypyridyloxy (e.g., 2-carboxy-4-pyridyloxy etc.), carboxypyridazinyloxy (e.g., 3-carboxy-5-pyridazinyloxy etc.), carboxypyrimidinyloxy (e.g., 2-carboxy-4-pyrimidinyloxy etc.), carboxypyrazinyloxy (e.g., 2-carboxy-6-pyrazinyloxy etc.) and the like.

In the present specification, the C1-C4 alkoxy-carbonyl-substituted 5- or 6-membered heteroaryloxy group means a 5- or 6-membered heteroaryloxy group wherein a C1-C4 alkoxy-carbonyl group is substituted at a substitutable position of the 5- or 6-membered heteroaryl ring. Specific preferable examples thereof include
methoxycarbonylpyrrolyloxy (e.g., 2-methoxycarbonyl-4-pyrrolyloxy etc.), ethoxycarbonylpyrrolyloxy (e.g., 2-ethoxycarbonyl-4-pyrrolyloxy etc.), propoxycarbonylpyrrolyloxy (e.g., 2-propoxycarbonyl-4-pyrrolyloxy etc.), isopropoxycarbonylpyrrolyloxy (e.g., 2-isopropoxycarbonyl-4-pyrrolyloxy etc.), butoxycarbonylpyrrolyloxy (e.g., 2-butoxycarbonyl-4-pyrrolyloxy etc.), sec-butoxycarbonylpyrrolyloxy (e.g., 2-sec-butoxycarbonyl-4-pyrrolyloxy etc.), isobutoxycarbonylpyrrolyloxy (e.g., 2-isobutoxycarbonyl-4-pyrrolyloxy etc.), tert-butoxycarbonylpyrrolyloxy (e.g., 2-tert-butoxycarbonyl-4-pyrrolyloxy etc.);
methoxycarbonylfuryloxy (e.g., 2-methoxycarbonyl-4-furyloxy etc.), ethoxycarbonylfuryloxy (e.g., 2-methoxycarbonyl-4-furyloxy etc.), propoxycarbonylfuryloxy (e.g., 2-propoxycarbonyl-4-furyloxy etc.), isopropoxycarbonylfuryloxy (e.g., 2-isopropoxycarbonyl-4-furyloxy etc.), butoxycarbonylfuryloxy (e.g., 2-butoxycarbonyl-4-furyloxy etc.), sec-butoxycarbonylfuryloxy (e.g., 2-sec-butoxycarbonyl-4-furyloxy etc.), isobutoxycarbonylfuryloxy (e.g., 2-isobutoxycarbonyl-4-furyloxy etc.), tert-butoxycarbonylfuryloxy (e.g., 2-tert-butoxycarbonyl-4-furyloxy etc.);

methoxycarbonylthienyloxy (e.g., 2-methoxycarbonyl-4-thienyloxy etc.), ethoxycarbonylthienyloxy (e.g., 2-ethoxycarbonyl-4-thienyloxy etc.), propoxycarbonylthienyloxy (e.g., 2-propoxycarbonyl-4-thienyloxy etc.), isopropoxycarbonylthienyloxy (e.g., 2-isopropoxycarbonyl-4-thienyloxy etc.), butoxycarbonylthienyloxy (e.g., 2-butoxycarbonyl-4-thienyloxy etc.), sec-butoxycarbonylthienyloxy (e.g., 2-sec-butoxycarbonyl-4-thienyloxy etc.), isobutoxycarbonylthienyloxy (e.g., 2-isobutoxycarbonyl-4-thienyloxy etc.), tert-butoxycarbonylthienyloxy (e.g., 2-tert-butoxycarbonyl-4-thienyloxy etc.);

methoxycarbonylimidazolyloxy (e.g., 2-methoxycarbonyl-4-imidazolyloxy etc.), ethoxycarbonylimidazolyloxy (e.g., 2-ethoxycarbonyl-4-imidazolyloxy etc.), propoxycarbonylimidazolyloxy (e.g., 2-propoxycarbonyl-4-imidazolyloxy etc.), isopropoxycarbonylimidazolyloxy (e.g., 2-isopropoxycarbonyl-4-imidazolyloxy etc.), butoxycarbonylimidazolyloxy (e.g., 2-butoxycarbonyl-4-imidazolyloxy etc.), sec-butoxycarbonylimidazolyloxy (e.g., 2-sec-butoxycarbonyl-4-imidazolyloxy etc.), isobutoxycarbonylimidazolyloxy (e.g., 2-isobutoxycarbonyl-4-imidazolyloxy etc.), tert-butoxycarbonylimidazolyloxy (e.g., 2-tert-butoxycarbonyl-4-imidazolyloxy etc.);

methoxycarbonyloxazolyloxy (e.g., 2-methoxycarbonyl-4-oxazolyloxy etc.), ethoxycarbonyloxazolyloxy (e.g., 2-ethoxycarbonyl-4-oxazolyloxy etc.), propoxycarbonyloxazolyloxy (e.g., 2-propoxycarbonyl-4-oxazolyloxy etc.), isopropoxycarbonyloxazolyloxy (e.g., 2-isopropoxycarbonyl-4-oxazolyloxy etc.), butoxycarbonyloxazolyloxy (e.g., 2-butoxycarbonyl-4-oxazolyloxy etc.), sec-butoxycarbonyloxazolyloxy (e.g., 2-sec-butoxycarbonyl-4-oxazolyloxy etc.), isobutoxycarbonyloxazolyloxy (e.g., 2-isobutoxycarbonyl-4-oxazolyloxy etc.), tert-butoxycarbonyloxazolyloxy (e.g., 2-tert-butoxycarbonyl-4-oxazolyloxy etc.);

methoxycarbonylthiazolyloxy (e.g., 2-methoxycarbonyl-4-thiazolyloxy etc.), ethoxycarbonylthiazolyloxy (e.g., 2-ethoxycarbonyl-4-thiazolyloxy etc.), propoxycarbonylthiazolyloxy (e.g., 2-propoxycarbonyl-4-thiazolyloxy etc.), isopropoxycarbonylthiazolyloxy (e.g., 2-isopropoxycarbonyl-4-thiazolyloxy etc.), butoxycarbonylthiazolyloxy (e.g., 2-butoxycarbonyl-4-thiazolyloxy etc.), sec-butoxycarbonylthiazolyloxy (e.g., 2-sec-butoxycarbonyl-4-thiazolyloxy etc.), isobutoxycarbonylthiazolyloxy (e.g., 2-isobutoxycarbonyl-4-thiazolyloxy etc.), tert-butoxycarbonylthiazolyloxy (e.g., 2-tert-butoxycarbonyl-4-thiazolyloxy etc.);

methoxycarbonylpyrazolyloxy (e.g., 3-methoxycarbonyl-5-pyrazolyloxy etc.), ethoxycarbonylpyrazolyloxy (e.g., 3-ethoxycarbonyl-5-pyrazolyloxy etc.), propoxycarbonylpyrazolyloxy (e.g., 3-propoxycarbonyl-5-pyrazolyloxy etc.), isopropoxycarbonylpyrazolyloxy (e.g., 3-isopropoxycarbonyl-5-pyrazolyloxy etc.), butoxycarbonylpyrazolyloxy (e.g., 3-butoxycarbonyl-5-pyrazolyloxy etc.), sec-butoxycarbonylpyrazolyloxy (e.g., 3-sec-butoxycarbonyl-5-pyrazolyloxy etc.), isobutoxycarbonylpyrazolyloxy (e.g., 3-isobutoxycarbonyl-5-pyrazolyloxy etc.), tert-butoxycarbonylpyrazolyloxy (e.g., 3-tert-butoxycarbonyl-5-pyrazolyloxy etc.);

methoxycarbonylisooxazolyloxy (e.g., 3-methoxycarbonyl-5-isooxazolyloxy etc.), ethoxycarbonylisooxazolyloxy (e.g., 3-ethoxycarbonyl-5-isooxazolyloxy etc.), propoxycarbonylisooxazolyloxy (e.g., 3-propoxycarbonyl-5-isooxazolyloxy etc.), isopropoxycarbonylisooxazolyloxy (e.g., 3-isopropoxycarbonyl-5-isooxazolyloxy etc.), butoxycarbonylisooxazolyloxy (e.g., 3-butoxycarbonyl-5-isooxazolyloxy etc.), sec-butoxycarbonylisooxazolyloxy (e.g., 3-sec-butoxycarbonyl-5-isooxazolyloxy etc.), isobutoxycarbonylisooxazolyloxy (e.g., 3-isobutoxycarbonyl-5-isooxazolyloxy etc.), tert-butoxycarbonylisooxazolyloxy (e.g., 3-tert-butoxycarbonyl-5-isooxazolyloxy etc.);

methoxycarbonylisothiazolyloxy (e.g., 3-methoxycarbonyl-5-isothiazolyloxy etc.), ethoxycarbonylisothiazolyloxy (e.g., 3-ethoxycarbonyl-5-isothiazolyloxy etc.), propoxycarbonylisothiazolyloxy (e.g., 3-propoxycarbonyl-5-isothiazolyloxy etc.), isopropoxycarbonylisothiazolyloxy (e.g., 3-isopropoxycarbonyl-5-isothiazolyloxy etc.), butoxycarbonylisothiazolyloxy (e.g., 3-butoxycarbonyl-5-isothiazolyloxy etc.), sec-butoxycarbonylisothiazolyloxy (e.g., 3-sec-butoxycarbonyl-5-isothiazolyloxy etc.), isobutoxycarbonylisothiazolyloxy (e.g., 3-isobutoxycarbonyl-5-isothiazolyloxy etc.), tert-butoxycarbonylisothiazolyloxy (e.g., 3-tert-butoxycarbonyl-5-isothiazolyloxy etc.);

methoxycarbonylpyridyloxy (e.g., 2-methoxycarbonyl-4-pyridyloxy etc.), ethoxycarbonylpyridyloxy (e.g., 2-ethoxycarbonyl-4-pyridyloxy etc.), propoxycarbonylpyridyloxy (e.g., 2-propoxycarbonyl-4-pyridyloxy etc.), isopropoxycarbonylpyridyloxy (e.g., 2-isopropoxycarbonyl-4-pyridyloxy etc.), butoxycarbonylpyridyloxy (e.g., 2-butoxycarbonyl-4-pyridyloxy etc.), sec-butoxycarbonylpyridyloxy (e.g., 2-sec-butoxycarbonyl-4-pyridyloxy etc.), isobutoxycarbonylpyridyloxy (e.g., 2-isobutoxycarbonyl-4-pyridyloxy etc.), tert-butoxycarbonylpyridyloxy (e.g., 2-tert-butoxycarbonyl-4-pyridyloxy etc.);

methoxycarbonylpyridazinyloxy (e.g., 3-methoxycarbonyl-5-pyridazinyloxy etc.), ethoxycarbonylpyridazinyloxy (e.g., 3-ethoxycarbonyl-5-pyridazinyloxy etc.), propoxycarbonylpyridazinyloxy (e.g., 3-propoxycarbonyl-5-pyridazinyloxy etc.), isopropoxycarbonylpyridazinyloxy (e.g., 3-isopropoxycarbonyl-5-pyridazinyloxy etc.), butoxycarbonylpyridazinyloxy (e.g., 3-butoxycarbonyl-5-pyridazinyloxy etc.), sec-butoxycarbonylpyridazinyloxy (e.g., 3-sec-butoxycarbonyl-5-pyridazinyloxy etc.), isobutoxycarbonylpyridazinyloxy (e.g., 3-isobutoxycarbonyl-5-pyridazinyloxy etc.), tert-butoxycarbonylpyridazinyloxy (e.g., 3-tert-butoxycarbonyl-5-pyridazinyloxy etc.);

methoxycarbonylpyrimidinyloxy (e.g., 2-methoxycarbonyl-4-pyrimidinyloxy etc.), ethoxycarbonylpyrimidinyloxy (e.g., 2-ethoxycarbonyl-4-pyrimidinyloxy etc.), propoxycarbonylpyrimidinyloxy (e.g., 2-propoxycarbonyl-4-pyrimidinyloxy etc.), isopropoxycarbonylpyrimidinyloxy (e.g., 2-isopropoxycarbonyl-4-pyrimidinyloxy etc.), butoxycarbonylpyrimidinyloxy (e.g., 2-butoxycarbonyl-4-pyrimidinyloxy etc.), sec-butoxycarbonylpyrimidinyloxy (e.g., 2-sec-butoxycarbonyl-4-pyrimidinyloxy etc.), isobutoxycarbonylpyrimidinyloxy (e.g., 2-isobutoxycarbonyl-4-pyrimidinyloxy etc.), tert-butoxycarbonylpyrimidinyloxy (e.g., 2-tert-butoxycarbonyl-4-pyrimidinyloxy etc.);

methoxycarbonylpyrazinyloxy (e.g., 2-methoxycarbonyl-6-pyrazinyloxy etc.), ethoxycarbonylpyrazinyloxy (e.g., 2-ethoxycarbonyl-6-pyrazinyloxy etc.), propoxycarbonylpyrazinyloxy (e.g., 2-propoxycarbonyl-6-pyrazinyloxy etc.), isopropoxycarbonylpyrazinyloxy (e.g., 2-isopropoxycarbonyl-6-pyrazinyloxy etc.), butoxycarbonylpyrazinyloxy (e.g., 2-butoxycarbonyl-6-pyrazinyloxy etc.), sec-butoxycarbonylpyrazinyloxy (e.g., 2-sec-butoxycarbonyl-6-pyrazinyloxy etc.), isobutoxycarbonylpyrazinyloxy (e.g., 2-isobutoxycarbonyl-6-pyrazinyloxy etc.), tert-butoxycarbonylpyrazinyloxy (e.g., 2-tert-butoxycarbonyl-6-pyrazinyloxy etc.);
and the like.

In the present specification, the carbamoyl-substituted 5- or 6-membered heteroaryloxy group means a 5- or 6-membered heteroaryloxy group wherein a carbamoyl group is substituted at a substitutable position of the 5- or 6-membered heteroaryl ring. Specific preferable examples thereof include carbamoylpyrrolyloxy (e.g., 2-carbamoyl-4-pyrrolyloxy etc.), carbamoylfuryloxy (e.g., 2-carbamoyl-4-furyloxy etc.), carbamoylthienyloxy (e.g., 2-carbamoyl-4-thienyloxy etc.), carbamoylimidazolyloxy (e.g., 2-carbamoyl-4-imidazolyloxy etc.), carbamoyloxazolyloxy (e.g., 2-carbamoyl-4-oxazolyloxy etc.), carbamoylthiazolyloxy (e.g., 2-carbamoyl-4-thiazolyloxy etc.), carbamoylpyrazolyloxy (e.g., 3-carbamoyl-5-pyrazolyloxy etc.), carbamoylisooxazolyloxy (e.g., 3-carbamoyl-5-isooxazolyloxy etc.), carbamoylisothiazolyloxy (e.g., 3-carbamoyl-5-isothiazolyloxy etc.), carbamoylpyridyloxy (e.g., 2-carbamoyl-4-pyridyloxy etc.), carbamoylpyridazinyloxy (e.g., 3-carbamoyl-5-pyridazinyloxy etc.), carbamoylpyrimidinyloxy (e.g., 2-carbamoyl-4-pyrimidinyloxy etc.), carbamoylpyrazinyloxy (e.g., 2-carbamoyl-6-pyrazinyloxy etc.) and the like.

In the present specification, the C1-C4 alkyl-carbamoyl-substituted 5- or 6-membered heteroaryloxy group means a 5- or 6-membered heteroaryloxy group wherein a C1-C4 alkyl-carbamoyl group is substituted at a substitutable position of the 5- or 6-membered heteroaryl ring. Specific preferable examples thereof include
methylcarbamoylpyrrolyloxy (e.g., 2-methylcarbamoyl-4-pyrrolyloxy etc.), ethylcarbamoylpyrrolyloxy (e.g., 2-ethylcarbamoyl-4-pyrrolyloxy etc.), propylcarbamoylpyrrolyloxy (e.g., 2-propylcarbamoyl-4-pyrrolyloxy etc.), isopropylcarbamoylpyrrolyloxy (e.g., 2-isopropylcarbamoyl-4-pyrrolyloxy etc.), butylcarbamoylpyrrolyloxy (e.g., 2-butylcarbamoyl-4-pyrrolyloxy etc.), sec-butylcarbamoylpyrrolyloxy (e.g., 2-sec-butylcarbamoyl-4-pyrrolyloxy etc.), isobutylcarbamoylpyrrolyloxy (e.g., 2-isobutylcarbamoyl-4-pyrrolyloxy etc.), tert-butylcarbamoylpyrrolyloxy (e.g., 2-tert-butylcarbamoyl-4-pyrrolyloxy etc.);
methylcarbamoylfuryloxy (e.g., 2-methylcarbamoyl-4-furyloxy etc.), ethylcarbamoylfuryloxy (e.g., 2-ethylcarbamoyl-4-furyloxy etc.), propylcarbamoylfuryloxy (e.g., 2-propylcarbamoyl-4-furyloxy etc.), isopropylcarbamoylfuryloxy (e.g., 2-isopropylcarbamoyl-4-furyloxy etc.), butylcarbamoylfuryloxy (e.g., 2-butylcarbamoyl-4-furyloxy etc.), sec-butylcarbamoylfuryloxy (e.g., 2-sec-butylcarbamoyl-4-furyloxy etc.), isobutylcarbamoylfuryloxy (e.g., 2-isobutylcarbamoyl-4-furyloxy etc.), tert-butylcarbamoylfuryloxy (e.g., 2-tert-butylcarbamoyl-4-furyloxy etc.);
methylcarbamoylthienyloxy (e.g., 2-methylcarbamoyl-4-thienyloxy etc.), ethylcarbamoylthienyloxy (e.g., 2-ethylcarbamoyl-4-thienyloxy etc.), propylcarbamoylthienyloxy (e.g., 2-propylcarbamoyl-4-thienyloxy etc.), isopropylcarbamoylthienyloxy (e.g., 2-isopropylcarbamoyl-4-thienyloxy etc.), butylcarbamoylthienyloxy (e.g., 2-butylcarbamoyl-4-thienyloxy etc.), sec-butylcarbamoylthienyloxy (e.g., 2-sec-butylcarbamoyl-4-thienyloxy etc.), isobutylcarbamoylthienyloxy (e.g., 2-isobutylcarbamoyl-4-thienyloxy etc.), tert-butylcarbamoylthienyloxy (e.g., 2-tert-butylcarbamoyl-4-thienyloxy etc.);
methylcarbamoylimidazolyloxy (e.g., 2-methylcarbamoyl-4-imidazolyloxy etc.), ethylcarbamoylimidazolyloxy (e.g., 2-ethylcarbamoyl-4-imidazolyloxy etc.), propylcarbamoylimidazolyloxy (e.g., 2-propylcarbamoyl-4-imidazolyloxy etc.), isopropylcarbamoylimidazolyloxy (e.g., 2-isopropylcarbamoylcarbonyl-4-imidazolyloxy etc.), butylcarbamoylimidazolyloxy (e.g., 2-butylcarbamoyl-4-imidazolyloxy etc.), sec-butylcarbamoylimidazolyloxy (e.g., 2-sec-butylcarbamoyl-4-imidazolyloxy etc.), isobutylcarbamoylimidazolyloxy (e.g., 2-isobutylcarbamoyl-4-imidazolyloxy etc.), tert-butylcarbamoylimidazolyloxy (e.g., 2-tert-butylcarbamoyl-4-imidazolyloxy etc.);
methylcarbamoyloxazolyloxy (e.g., 2-methylcarbamoyl-4-oxazolyloxy etc.), ethylcarbamoyloxazolyloxy (e.g., 2-ethylcarbamoyl-4-oxazolyloxy etc.), propylcarbamoyloxazolyloxy (e.g., 2-propylcarbamoyl-4-oxazolyloxy etc.), isopropylcarbamoyloxazolyloxy (e.g., 2-isopropylcarbamoyl-4-oxazolyloxy etc.), butylcarbamoyloxazolyloxy (e.g., 2-butylcarbamoyl-4-oxazolyloxy etc.), sec-butylcarbamoyloxazolyloxy (e.g., 2-sec-butylcarbamoyl-4-oxazolyloxy etc.), isobutylcarbamoyloxazolyloxy (e.g., 2-isobutylcarbamoyl-4-oxazolyloxy etc.), tert-butylcarbamoyloxazolyloxy (e.g., 2-tert-butylcarbamoyl-4-oxazolyloxy etc.);
methylcarbamoylthiazolyloxy (e.g., 2-methylcarbamoyl-4-thiazolyloxy etc.), ethylcarbamoylthiazolyloxy (e.g., 2-ethylcarbamoyl-4-thiazolyloxy etc.), propylcarbamoylthiazolyloxy (e.g., 2-propylcarbamoyl-4-thiazolyloxy etc.), isopropylcarbamoylthiazolyloxy (e.g., 2-isopropylcarbamoyl-4-thiazolyloxy etc.), butylcarbamoylthiazolyloxy (e.g., 2-butylcarbamoyl-4-thiazolyloxy etc.), sec-butylcarbamoylthiazolyloxy (e.g., 2-sec-butylcarbamoyl-4-thiazolyloxy etc.), isobutylcarbamoylthiazolyloxy (e.g., 2-isobutylcarbamoyl-4-thiazolyloxy etc.), tert-butylcarbamoylthiazolyloxy (e.g., 2-tert-butylcarbamoyl-4-thiazolyloxy etc.);
methylcarbamoylpyrazolyloxy (e.g., 3-methylcarbamoyl-5-pyrazolyloxy etc.), ethylcarbamoylpyrazolyloxy (e.g., 3-ethylcarbamoyl-5-pyrazolyloxy etc.), propylcarbamoylpyrazolyloxy (e.g., 3-propylcarbamoyl-5-pyrazolyloxy etc.), isopropylcarbamoylpyrazolyloxy (e.g., 3-isopropylcarbamoyl-5-pyrazolyloxy etc.), butylcarbamoylpyrazolyloxy (e.g., 3-butylcarbamoyl-5-pyrazolyloxy etc.), sec-butylcarbamoylpyrazolyloxy (e.g., 3-sec-butylcarbamoyl-5-pyrazolyloxy etc.), isobutylcarbamoylpyrazolyloxy (e.g., 3-isobutylcarbamoyl-5-pyrazolyloxy etc.), tert-butylcarbamoylpyrazolyloxy (e.g., 3-tert-butylcarbamoyl-5-pyrazolyloxy etc.);
methylcarbamoylisooxazolyloxy (e.g., 3-methylcarbamoyl-5-isooxazolyloxy etc.), ethylcarbamoylisooxazolyloxy (e.g., 3-ethylcarbamoyl-5-isooxazolyloxy etc.), propylcarbamoylisooxazolyloxy (e.g., 3-propylcarbamoyl-5-isooxazolyloxy etc.), isopropylcarbamoylisooxazolyloxy (e.g., 3-isopropylcarbamoyl-5-isooxazolyloxy etc.), butylcarbamoylisooxazolyloxy (e.g., 3-butylcarbamoyl-5-isooxazolyloxy etc.), sec-butylcarbamoylisooxazolyloxy (e.g., 3-sec-butylcarbamoyl-5-isooxazolyloxy etc.), isobutylcarbamoylisooxazolyloxy (e.g., 3-isobutylcarbamoyl-5-isooxazolyloxy etc.), tert-butylcarbamoylisooxazolyloxy (e.g., 3-tert-butylcarbamoyl-5-isooxazolyloxy etc.);
methylcarbamoylisothiazolyloxy (e.g., 3-methylcarbamoyl-5-isothiazolyloxy etc.), ethylcarbamoylisothiazolyloxy (e.g., 3-ethylcarbamoyl-5-isothiazolyloxy etc.), propylcarbamoylisothiazolyloxy (e.g., 3-propylcarbamoyl-5-isothiazolyloxy etc.), isopropylcarbamoylisothiazolyloxy (e.g., 3-isopropylcarbamoyl-5-isothiazolyloxy etc.), butylcarbamoylisothiazolyloxy (e.g., 3-butylcarbamoyl-5-isothiazolyloxy etc.), sec-butylcarbamoylisothiazolyloxy (e.g., 3-sec-butylcarbamoyl-5-isothiazolyloxy etc.), isobutylcarbamoylisothiazolyloxy (e.g., 3-isobutylcarbamoyl-5-isothiazolyloxy etc.), tert-butylcarbamoylisothiazolyloxy (e.g., 3-tert-butylcarbamoyl-5-isothiazolyloxy etc.);
methylcarbamoylpyridyloxy (e.g., 2-methylcarbamoyl-4-pyridyloxy etc.), ethylcarbamoylpyridyloxy (e.g., 2-ethylcarbamoyl-4-pyridyloxy etc.), propylcarbamoylpyridyloxy (e.g., 2-propylcarbamoyl-4-pyridyloxy etc.), isopropylcarbamoylpyridyloxy (e.g., 2-isopropylcarbamoyl-4-pyridyloxy etc.), butylcarbamoylpyridyloxy (e.g., 2-butylcarbamoyl-4-pyridyloxy etc.), sec-butylcarbamoylpyridyloxy (e.g., 2-sec-butylcarbamoyl-4-pyridyloxy etc.), isobutylcarbamoylpyridyloxy (e.g., 2-isobutylcarbamoyl-4-pyridyloxy etc.), tert-butylcarbamoylpyridyloxy (e.g., 2-tert-butylcarbamoyl-4-pyridyloxy etc.);
methylcarbamoylpyridazinyloxy (e.g., 3-methylcarbamoyl-5-pyridazinyloxy etc.), ethylcarbamoylpyridazinyloxy (e.g., 3-ethylcarbamoyl-5-pyridazinyloxy etc.), propylcarbamoylpyridazinyloxy (e.g., 3-propylcarbamoyl-5-pyridazinyloxy etc.), isopropylcarbamoylpyridazinyloxy (e.g., 3-isopropylcarbamoyl-5-pyridazinyloxy etc.), butylcarbamoylpyridazinyloxy (e.g., 3-butylcarbamoyl-5-pyridazinyloxy etc.), sec-butylcarbamoylpyridazinyloxy (e.g., 3-sec-butylcarbamoyl-5-pyridazinyloxy etc.), isobutylcarbamoylpyridazinyloxy (e.g., 3-isobutylcarbamoyl-5-pyridazinyloxy etc.), tert-butylcarbamoylpyridazinyloxy (e.g., 3-tert-butylcarbamoyl-5-pyridazinyloxy etc.);
methylcarbamoylpyrimidinyloxy (e.g., 2-methylcarbamoyl-4-pyrimidinyloxy etc.), ethylcarbamoylpyrimidinyloxy (e.g., 2-ethylcarbamoyl-4-pyrimidinyloxy etc.), propylcarbamoylpyrimidinyloxy (e.g., 2-propylcarbamoyl-4-pyrimidinyloxy etc.), isopropylcarbamoylpyrimidinyloxy (e.g., 2-isopropylcarbamoyl-4-pyrimidinyloxy etc.), butylcarbamoylpyrimidinyloxy (e.g., 2-butylcarbamoyl-4-pyrimidinyloxy etc.), sec-butylcarbamoylpyrimidinyloxy (e.g., 2-sec-butylcarbamoyl-4-pyrimidinyloxy etc.), isobutylcarbamoylpyrimidinyloxy (e.g., 2-isobutylcarbamoyl-4-pyrimidinyloxy etc.), tert-butylcarbamoylpyrimidinyloxy (e.g., 2-tert-butylcarbamoyl-4-pyrimidinyloxy etc.);
methylcarbamoylpyrazinyloxy (e.g., 2-methylcarbamoyl-6-pyrazinyloxy etc.), ethylcarbamoylpyrazinyloxy (e.g., 2-ethylcarbamoyl-6-pyrazinyloxy etc.), propylcarbamoylpyrazinyloxy (e.g., 2-propylcarbamoyl-6-pyrazinyloxy etc.), isopropylcarbamoylpyrazinyloxy (e.g., 2-isopropylcarbamoyl-6-pyrazinyloxy etc.), butylcarbamoylpyrazinyloxy (e.g., 2-butylcarbamoyl-6-pyrazinyloxy etc.), sec-butylcarbamoylpyrazinyloxy (e.g., 2-sec-butylcarbamoyl-6-pyrazinyloxy etc.), isobutylcarbamoylpyrazinyloxy (e.g., 2-isobutylcarbamoyl-6-pyrazinyloxy etc.), tert-butylcarbamoylpyrazinyloxy (e.g., 2-tert-butylcarbamoyl-6-pyrazinyloxy etc.);
and the like.

In the present specification, the aryl group means an aromatic hydrocarbon group having a carbon number of 6-14. Specific preferable examples thereof include phenyl, naphthyl, anthryl, phenanthryl and the like.

In the present specification, the aryloxy group means —O— to which an aryl group is bonded. Specific preferable examples thereof include phenyloxy, naphthyloxy, anthryloxy, phenanthryloxy and the like.

In the present specification, the carboxy-substituted aryloxy group means an aryloxy group wherein a carboxy group is substituted at a substitutable position of the benzene ring. Specific preferable examples thereof include carboxyphenyloxy (e.g., 3-carboxyphenyloxy etc.), carboxynaphthyloxy (e.g., 3-carboxynaphthyloxy etc.), carboxyanthryloxy (e.g., 3-carboxyanthryloxy etc.), carboxyphenanthryloxy (e.g., 3-carboxyphenanthryloxy etc.) and the like.

In the present specification, the C1-C4 alkoxy-carbonyl-substituted aryloxy group means an aryloxy group wherein a C1-C4 alkoxy-carbonyl group is substituted at a substitutable position of the benzene ring. Specific preferable examples thereof include methoxycarbonylphenyloxy (e.g., 3-methoxycarbonylphenyloxy etc.), ethoxycarbonylphenyloxy (e.g., 3-ethoxycarbonylphenyloxy etc.), propoxycarbonylphenyloxy (e.g., 3-propoxycarbonylphenyloxy etc.), isopropoxycarbonylphenyloxy (e.g., 3-isopropoxycarbonylphenyloxy etc.), butoxycarbonylphenyloxy (e.g., 3-butoxycarbonylphenyloxy etc.), sec-butoxycarbonylphenyloxy (e.g., 3-sec-butoxycarbonylphenyloxy etc.), isobutoxycarbonylphenyloxy (e.g., 3-isobutoxycarbonylphenyloxy etc.), tert-butoxycarbonylphenyloxy (e.g., 3-tert-butoxycarbonylphenyloxy etc.), methoxycarbonylnaphthyloxy (e.g., 3-methoxycarbonylnaphthyloxy etc.), ethoxycarbonylnaphthyloxy (e.g., 3-ethoxycarbonylnaphthyloxy etc.), propoxycarbonylnaphthyloxy (e.g., 3-propoxycarbonylnaphthyloxy etc.), isopropoxycarbonylnaphthyloxy (e.g., 3-isopropoxycarbonylnaphthyloxy etc.), butoxycarbonylnaphthyloxy (e.g., 3-butoxycarbonylnaphthyloxy etc.), sec-butoxycarbonylnaphthyloxy (e.g., 3-sec-butoxycarbonylnaphthyloxy etc.), isobutoxycarbonylnaphthyloxy (e.g., 3-isobutoxycarbonylnaphthyloxy etc.), tert-butoxycarbonylnaphthyloxy (e.g., 3-tert-butoxycarbonylnaphthyloxy etc.), methoxycarbonylanthryloxy (e.g., 3-methoxycarbonylanthryloxy etc.), ethoxycarbonylanthryloxy (e.g., 3-ethoxycarbonylanthryloxy etc.), propoxycarbonylanthryloxy (e.g., 3-propoxycarbonylanthryloxy etc.), isopropoxycarbonylanthryloxy (e.g., 3-isopropoxycarbonylanthryloxy etc.), butoxycarbonylanthryloxy (e.g., 3-butoxycarbonylanthryloxy etc.), sec-butoxycarbonylanthryloxy (e.g., 3-sec-butoxycarbonylanthryloxy etc.), isobutoxycarbonylanthryloxy (e.g., 3-isobutoxycarbonylanthryloxy etc.), tert-butoxycarbonylanthryloxy (e.g., 3-tert-butoxycarbonylanthryloxy etc.), methoxycarbonylphenanthryloxy (e.g., 3-methoxycarbonylphenanthryloxy etc.), ethoxycarbonylphenanthryloxy (e.g., 3-ethoxycarbonylphenanthryloxy etc.), propoxycarbonylphenanthryloxy (e.g., 3-propoxycarbonylphenanthryloxy etc.), isopropoxycarbonylphenanthryloxy (e.g., 3-isopropoxycarbonylphenanthryloxy etc.), butoxycarbonylphenanthryloxy (e.g., 3-butoxycarbonylphenanthryloxy etc.), sec-butoxycarbonylphenanthryloxy (e.g., 3-sec-butoxycarbonylphenanthryloxy etc.), isobutoxycarbonylphenanthryloxy (e.g., 3-isobutoxycarbonylphenanthryloxy etc.), tert-butoxycarbonylphenanthryloxy (e.g., 3-tert-butoxycarbonylphenanthryloxy etc.) and the like.

In the present specification, the carbamoyl-substituted aryloxy group means an aryloxy group wherein a carbamoyl group is substituted at a substitutable position of the benzene ring. Specific preferable examples thereof include carbamoylphenyloxy (e.g., 3-carbamoylphenyloxy etc.), carbamoylnaphthyloxy (e.g., 3-carbamoylnaphthyloxy etc.), carbamoylanthryloxy (e.g., 3-carbamoylanthryloxy etc.), carbamoylphenanthryloxy (e.g., 3-carbamoylphenanthryloxy etc.) and the like.

In the present specification, the C1-C4 alkyl-carbamoyl-substituted aryloxy group means an aryloxy group wherein a C1-C4 alkyl-carbamoyl group is substituted at a substitutable position of the benzene ring. Specific preferable examples thereof include methylcarbamoylphenyloxy (e.g., 3-methylcarbamoylphenyloxy etc.), ethylcarbamoylphenyloxy (e.g., 3-ethylcarbamoylphenyloxy etc.), propylcarbamoylphenyloxy (e.g., 3-propylcarbamoylphenyloxy etc.), isopropylcarbamoylphenyloxy (e.g., 3-isopropylcarbamoylphenyloxy etc.), butylcarbamoylphenyloxy (e.g., 3-butylcarbamoylphenyloxy etc.), sec-butylcarbamoylphenyloxy (e.g., 3-sec-butylcarbamoylphenyloxy etc.), isobutylcarbamoylphenyloxy (e.g., 3-isobutylcarbamoylphenyloxy etc.), tert-butylcarbamoylphenyloxy (e.g., 3-tert-butylcarbamoylphenyloxy etc.), methylcarbamoylnaphthyloxy (e.g., 3-methylcarbamoylnaphthyloxy etc.), ethylcarbamoylnaphthyloxy (e.g., 3-ethylcarbamoylnaphthyloxy etc.), propylcarbamoylnaphthyloxy (e.g., 3-propylcarbamoylnaphthyloxy etc.), isopropylcarbamoylnaphthyloxy (e.g., 3-isopropylcarbamoylnaphthyloxy etc.), butylcarbamoylnaphthyloxy (e.g., 3-butylcarbamoylnaphthyloxy etc.), sec-butylcarbamoylnaphthyloxy (e.g., 3-sec-butylcarbamoylnaphthyloxy etc.), isobutylcarbamoylnaphthyloxy (e.g., 3-isobutylcarbamoylnaphthyloxy etc.), tert-butylcarbamoylnaphthyloxy (e.g., 3-tert-butylcarbamoylnaphthyloxy etc.), methylcarbamoylanthryloxy (e.g., 3-methylcarbamoylanthryloxy etc.), ethylcarbamoylanthryloxy (e.g., 3-ethylcarbamoylanthryloxy etc.), propylcarbamoylanthryloxy (e.g., 3-propylcarbamoylanthryloxy etc.), isopropylcarbamoylanthryloxy (e.g., 3-isopropylcarbamoylanthryloxy etc.), butylcarbamoylanthryloxy (e.g., 3-butylcarbamoylanthryloxy etc.), sec-butylcarbamoylanthryloxy (e.g., 3-sec-butylcarbamoylanthryloxy etc.), isobutylcarbamoylanthryloxy (e.g., 3-isobutylcarbamoylanthryloxy etc.), tert-butylcarbamoylanthryloxy (e.g., 3-tert-butylcarbamoylanthryloxy etc.), methylcarbamoylphenanthryloxy (e.g., 3-methylcarbamoylphenanthryloxy etc.), ethylcarbamoylphenanthryloxy (e.g., 3-ethylcarbamoylphenanthryloxy etc.), propylcarbamoylphenanthryloxy (e.g., 3-propylcarbamoylphenanthryloxy etc.), isopropylcarbamoylphenanthryloxy (e.g., 3-isopropylcarbamoylphenanthryloxy etc.), butylcarbamoylphenanthryloxy (e.g., 3-butylcarbamoylphenanthryloxy etc.), sec-butylcarbamoylphenanthryloxy (e.g., 3-sec-butylcarbamoylphenanthryloxy etc.), isobutylcarbamoylphenanthryloxy (e.g., 3-isobutylcarbamoylphenanthryloxy etc.), tert-butylcarbamoylphenanthryloxy (e.g., 3-tert-butylcarbamoylphenanthryloxy etc.) and the like.

In the present invention, a preferable active ingredient of the prophylactic or therapeutic agent for ALS is a 1,3-diphenylurea derivative represented by the formula (1). Particularly, a 1,3-diphenylurea derivative wherein $R_1$ and $R_2$ are each independently a hydrogen atom, a halogen atom or a trifluoromethyl group and $R_3$ and $R_4$ are each independently a hydrogen atom, a halogen atom, or a C1-C4 alkyl-carbamoyl-substituted 5- or 6-membered heteroaryloxy group is preferable.

In the present invention, a more preferable active ingredient of the prophylactic or therapeutic agent for ALS is a 1,3-diphenylurea derivative represented by the formula (2), (3) or (4).

The 1,3-diphenylurea derivative to be used in the present invention may be a pharmaceutically acceptable salt. Pharmaceutically acceptable salts are well known to those of ordinary skill in the art, and preferable examples thereof include salts with inorganic acids such as hydrochloric acid, hydrobromic acid, nitric acid, sulfuric acid, phosphoric acid and the like; salts with organic acids such as formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like; alkali metal salts such as sodium salt, potassium salt and the like; alkaline earth metal salts such as calcium salt, magnesium salt, barium salt and the like; aluminum salt; ammonium salt; salts with organic bases such as trimethylamine, triethylamine, pyridine, picoline, 2,6-lutidine, ethanolamine, diethanolamine, triethanolamine, N,N-diethylamine, cyclohexylamine, N,N'-dicyclohexylamine, N,N'-dibenzylethylenediamine, N,N-dimethylaminopyridine (DMAP), 1,4-diazabicyclo[2.2.2]octane (DABCO), 1,5-diazabicyclo[4.3.0]nonene-5 (DBN), 1,8-diazabicyclo[5.4.0]undec-7-ene (DBU) and the like; salts with basic amino acids such as arginine, lysine, ornithine and the like; salts with acidic amino acids such as aspartic acid, glutamic acid and the like; and the like.

Some of the 1,3-diphenylurea derivatives to be used in the present invention can be prepared from a commercially available starting material by a known chemical reaction. Specifically, the following scheme can be provided.

When the 1,3-diphenylurea derivative has a functional group (amino group, hydroxyl group etc.), the functional group may be protected in advance as necessary, and subjected to deprotection by a conventional method after the above-mentioned reaction.

Examples of the amino-protecting group include formyl group, $C_{1-6}$ alkyl-carbonyl group, $C_{1-6}$ alkoxy-carbonyl group, benzoyl group, $C_{7-10}$ aralkyl-carbonyl group (e.g., benzylcarbonyl), $C_{7-14}$ aralkyloxy-carbonyl group (e.g., benzyloxycarbonyl, 9-fluorenylmethoxycarbonyl), trityl group, phthaloyl group, N,N-dimethylaminomethylene group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups may be substituted by 1 to 3 substituents selected from a halogen atom, a $C_{1-6}$ alkoxy group and a nitro group.

Examples of the hydroxy-protecting group include $C_{1-6}$ alkyl group, phenyl group, trityl group, $C_{7-10}$ aralkyl group (e.g., benzyl), formyl group, $C_{1-6}$ alkyl-carbonyl group, benzoyl group, $C_{7-10}$ aralkyl-carbonyl group (e.g., benzylcarbonyl), 2-tetrahydropyranyl group, 2-tetrahydrofuranyl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups may be substituted by 1 to 3 substituents selected from a halogen atom, a $C_{1-6}$ alkyl group, a $C_{1-6}$ alkoxy group and a nitro group.

The present invention also provides an agent for the prevention or treatment of ALS, containing a multikinase inhibitor. In the present specification, the multikinase inhibitor refers to a drug having an ability to inhibit two or more kinases selected from serine/treonine kinase such as MAP kinase, Mos/Raf kinase and the like and receptor tyrosine kinase. It is preferably a drug having at least a Raf inhibitory capacity, which is exemplified by the compound described in WO2000/042012. Preferred is sorafenib represented by the formula (4) and the like.

The prophylactic and/or therapeutic agent for ALS of the present invention can be administered orally or parenterally in the form of the active ingredient, a 1,3-diphenylurea derivative or multikinase inhibitor, as it is alone, or as a pharmaceutical composition in an appropriate dosage form blended with a pharmacologically acceptable carrier, excipient, diluent and the like.

As the composition for oral administration, solid or liquid dosage forms, specifically tablets (including sugar-coated tablets and film-coated tablets), pills, granules, powders, capsules (including soft capsules), syrups, emulsions, suspensions and the like can be mentioned. Meanwhile, as examples of the composition for parenteral administration, injections, suppositories and the like are used; the injections may include dosage forms such as intravenous injections, subcutaneous injections, intracutaneous injections, intramuscular injections and drip infusion injections. These formulations are produced by a well-known method using additives, including excipients (e.g., organic excipients like sugar derivatives such as lactose, sucrose, glucose, mannitol, and sorbitol; starch derivatives such as cornstarch, potato starch, α starch, and dextrin; cellulose derivatives such as crystalline cellulose; gum arabic; dextran; and pullulan; and inorganic excipients like silicate derivatives such as light silicic anhydride, synthetic aluminum silicate, calcium silicate, and magnesium metasilicoaluminate; phosphates such as calcium hydrogen phosphate; carbonates such as calcium carbonate; and sulfates such as calcium sulfate), lubricants (e.g., stearic acid, stearic acid metal salts such as calcium stearate and magnesium stearate; talc; colloidal silica; waxes such as beeswax and spermaceti; boric acid; adipic acid; sulfates such as sodium sulfate; glycol; fumaric acid; sodium benzoate; DL leucine; lauryl sulfates such as sodium lauryl sulfate and magnesium lauryl sulfate; silicates such as silicic anhydride and silicic hydrates; and the aforementioned starch derivatives), binders (e.g., hydroxypropylcellulose, hydroxypropylmethylcellulose, polyvinylpyrrolidone, macrogol, and the same compounds as the aforementioned excipients), disintegrants (e.g., cellulose derivatives such as low-substitutional hydroxypropylcellulose, carboxymethylcellulose, carboxymethylcellulose calcium, and internally crosslinked carboxymethylcellulose sodium; chemically modified starches and celluloses such as carboxymethylstarch, carboxymethylstarch sodium, and crosslinked polyvinylpyrrolidone), emulsifiers (e.g., colloidal clays such as bentonite and Veegum; metal hydroxides such as magnesium hydroxide and aluminum hydroxide; anionic surfactants such as sodium lauryl sulfate and calcium stearate; cationic surfactants such as benzalkonium chloride; and non-ionic surfactants such as polyoxyethylene alkyl ether, polyoxyethylene sorbitan fatty acid ester, and sucrose fatty acid ester), stabilizers (para-oxybenzoic acid esters such as methyl paraben and propyl paraben; alcohols such as chlorobutanol, benzyl alcohol, and phenylethyl alcohol; benzalkonium chloride; phenols such as phenol and cresol; thimerosal; dehydroacetic acid; and sorbic acid), taste/odor correctives (e.g., sweeteners, souring agents, and flavors in common use), and diluents.

While the dose of the 1,3-diphenylurea derivative or multikinase inhibitor as an active ingredient of the prophylactic and/or therapeutic agent for ALS in the present invention varies depending on the patient's symptoms, age, weight and other factors, it is at least 0.1 mg (suitably 0.5 mg) to at most 1000 mg (preferably 500 mg) per dose for oral administration, or at least 0.01 mg (preferably 0.05 mg) to at most 100 mg (preferably 50 mg) per dose for parenteral administration, and can be administered to an adult 1 to 6 times a day. The dose may be increased or reduced according to the symptoms.

Furthermore, the prophylactic and/or therapeutic agent for ALS of the present invention may be used in combination with other drugs, for example, glutamate action inhibitors (e.g., riluzole and the like), neurotrophic factors [e.g., insulin-like growth factor-1, 5-$HT_{1A}$ receptor agonists (e.g., xaliproden) and the like] and the like. The prophylactic and/or therapeutic agent for ALS of the present invention and these other drugs can be administered simultaneously, sequentially, or separately.

The present invention is hereinafter described in further detail by means of the following Examples, to which, however, the invention is not limited.

Examples

Human Neuroglioma Cell in which Luciferase Surrogates SOD1 Expression

A vector containing a DNA encoding secreted luciferase at the downstream of an SOD1 promoter was introduced into human neuroglioma H4 cell (ATCC) to prepare a cell line that extracellularly secretes luciferase protein on activation of SOD1 expression.

Influence of Candidate Drug on SOD1 Expression

Figure 1:
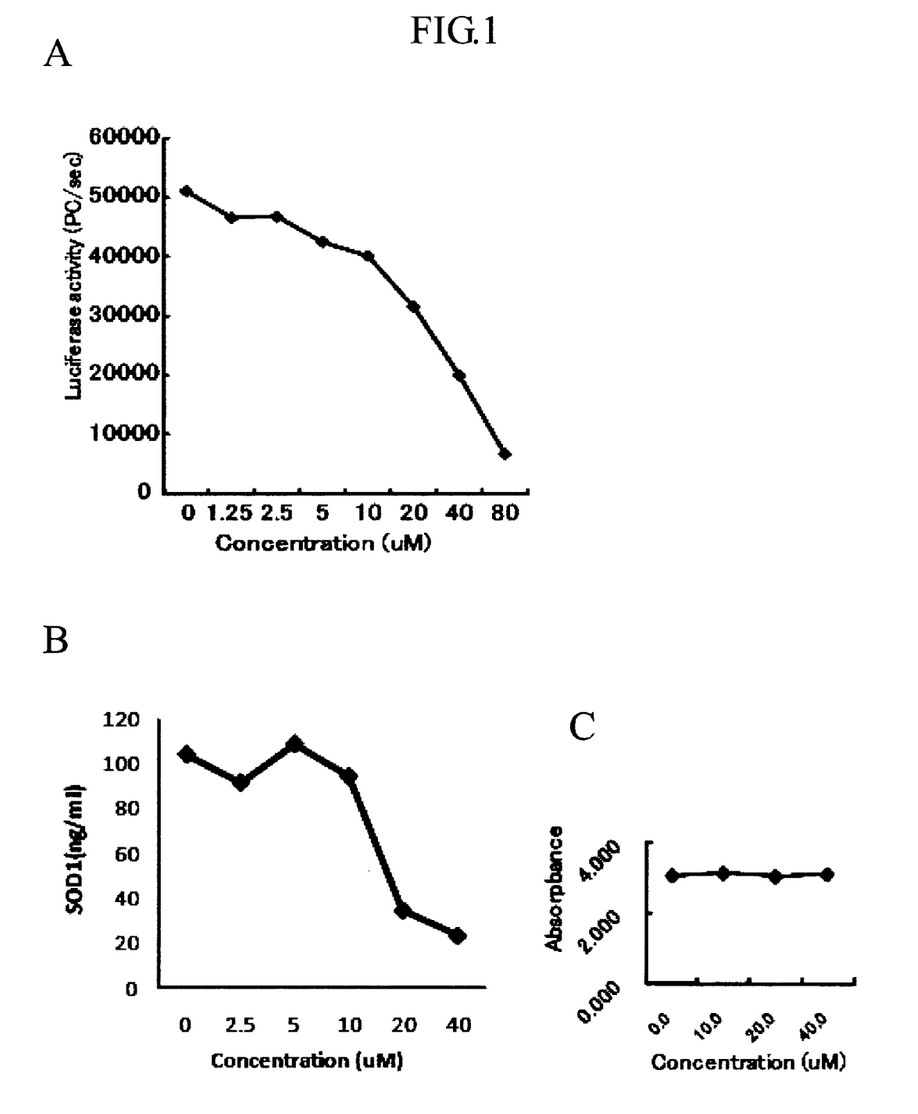
Figure 2:
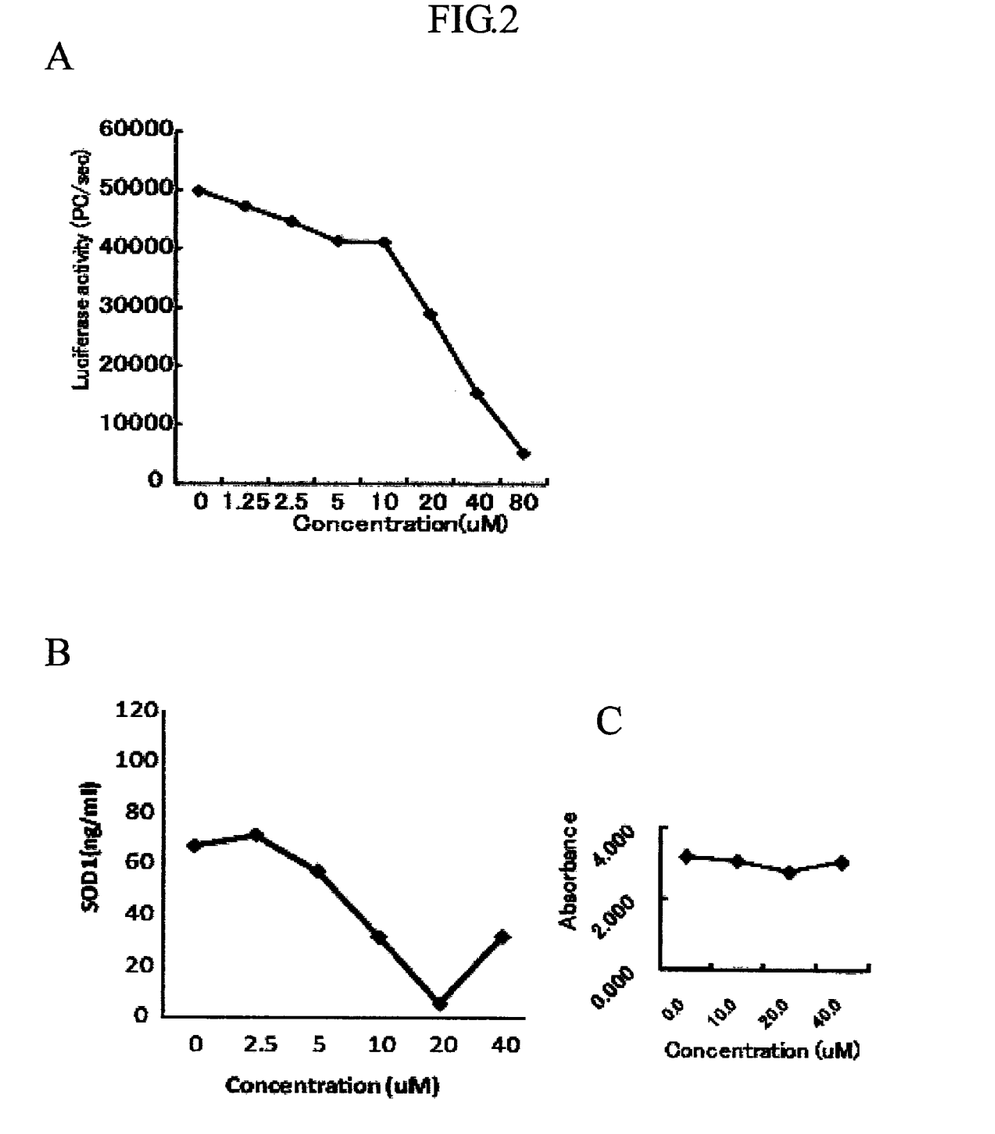
Figure 3:
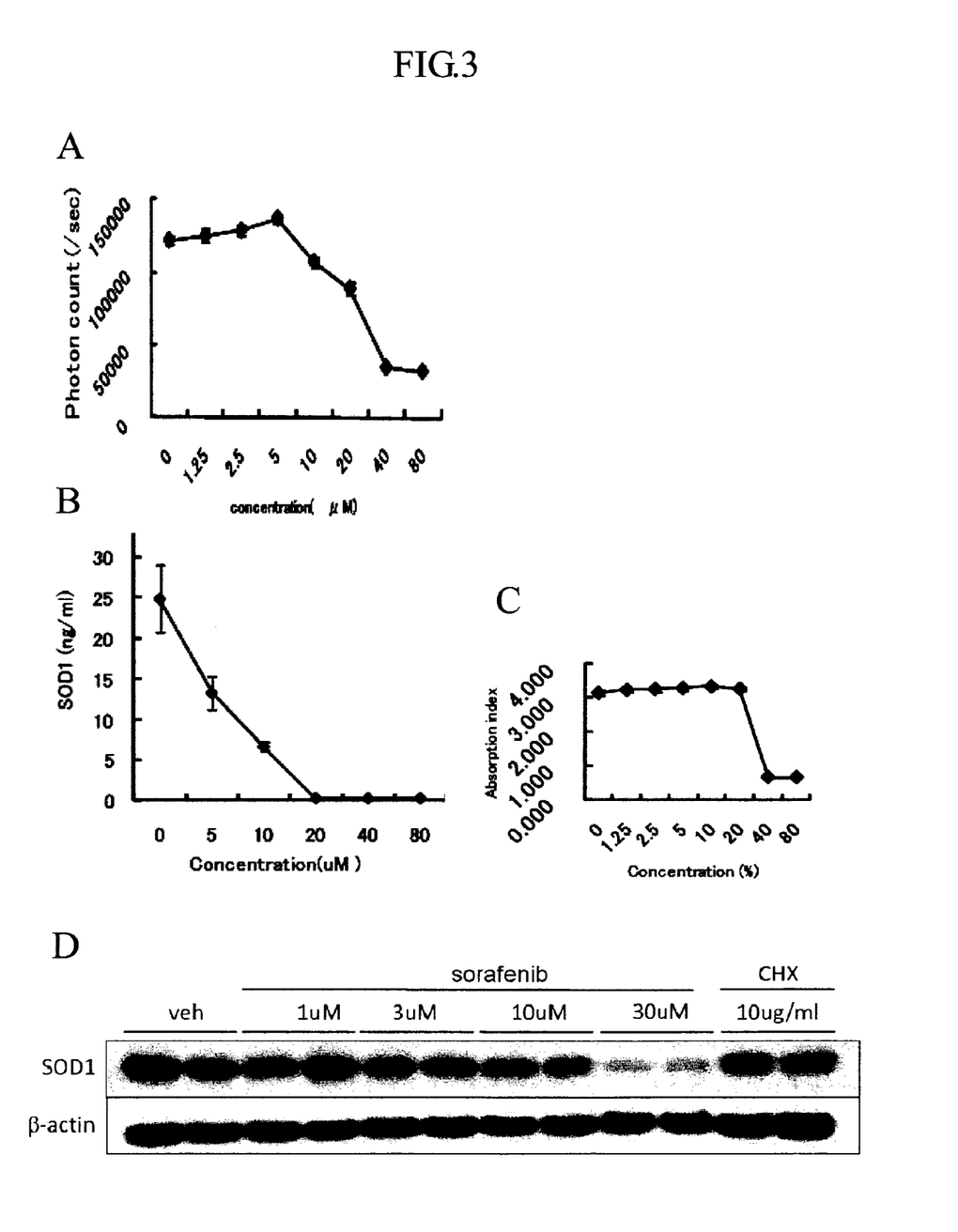

Urea and N-(3-fluorophenyl)-N'-[4-(trifluoromethyl)phenyl] (hereinafter UFTP) (CAS Registry Number: 695174-98-2), urea and N-(3-chlorophenyl)-N'-[4-(trifluoromethyl)phenyl] (hereinafter UCTP) (CAS Registry Number: 23751-05-5), and sorafenib tosylate (hereinafter sorafenib) (Toronto Research Chemicals) were added to the m aforementioned cell line at various concentrations, and the luciferase activity, SOD1 protein level (ELISA) and cell viability (WST-1) were examined. As a result, SOD1 expression was inhibited by not less than 10 µM of UFTP (FIG. 1B), not less than 5 µM of UCTP (FIG. 2 B), and not less than 5 µM of sorafenib (FIG. 3B).

Fibroblasts Derived from a Patient with Amyotrophic Lateral Sclerosis (ALS)

A 4-mm skin biopsy was cultured for 3 weeks, and the resulting cells in culture were used as the fibroblasts derived from an ALS patient.

Induction of iPS Cells

Human cDNAs for KLF4, Sox2, Oct3/4 and c-Myc were transferred to the above-described fibroblasts using a retrovirus, as described by Takahashi K et al. in Cell 131(5), 861, 2007. On day 6 after the gene transfer, the fibroblasts were transferred onto SNL feeder cells. The following day, the medium was replaced with a primate ES cell culture broth supplemented with 4 ng/ml of bFGF (Wako). The medium was exchanged every two days; 30 days after the gene transfer, colonies were picked up.

Formation of Neurospheres

Neurospheres were formed by a slightly modified version of the method described by Wada T et al. in PLoS ONE 4(8), e6722, 2009. Specifically, iPS cells were divided into small masses, and cultured in a dish coated with poly-L-lysine/laminin (PLL/LM) (Sigma-Aldrich) using the N2B27 medium (Gibco), which is prepared by adding 1% N2, 2% B27 and 200 µM glutamine to a culture broth of a 1:1 mixture of DMEM/F12 and the Neurobasal medium A. Furthermore, 100 ng/ml of Noggin was added to this medium. At 3-day intervals, the medium was replaced with a medium containing 100 ng/ml of Noggin; after 10 days of cultivation, the cells were passaged to a PLL/LM-coated dish. Subsequently, the medium was replaced with a medium containing 100 ng/ml of Noggin every other day. 7 days after the passage, the cells were seeded to a 2-hydroxyethylmetacrylate (HEMA)-coated dish at a cell density of 1,000,000 cells/ml. The medium used was an N2B27 medium supplemented with 20 ng/ml of EGF (R&D Systems), 20 ng/ml of bFGF and 50 ng/ml of heparin (Sigma-Aldrich). Passage was performed with pipetting at 30-day intervals; 1 ml of a fresh medium was added at 7-day intervals. All these culturing operations were performed by incubation at 37° C., 5% $CO_2$, in a moisturized atmosphere.

Induction of Differentiation into Astrocytes

Quaternary neurospheres were separated using Accutase, and seeded into an N2B27 medium containing 1% FBS (Japan Bio Serum), 10 ng/ml bone morphogenetic protein-4 (BMP-4) (R&D Systems) and 10 ng/ml leukemia inhibitory factor (LIF) (Alomone Labs) at a density of 50,000 cells/ml on a gelatin-coated dish. The medium was replaced with a fresh supply at 2-day intervals; 1 week later, the medium was replaced with a DMEM supplemented with 10% FBS and 1% penicillin/streptomycin. By this method, glial fibrillary acidic protein (GFAP)-positive cells were obtained, confirming the induction of differentiation into astrocytes.

Analysis of SOD1 in Astrocytes

The iPS cell-derived astrocytes were seeded to a 6-well plate at a density of 250,000 cells/well. After a vehicle [0.5% dimethylsulfoxide (DMSO)], cycloheximide at a concentration of 10 µg/ml, or sorafenib at various final concentrations (1 µM, 3 µM, 10 µM and 30 µM) were added, the plate was incubated for 48 hours. Subsequently, the cells were recovered, and lysed using a 20 mM Hepes, pH 7.4, containing 1% triton X-100, 10% glycerol, 5 mM EDTA, 120 mM NaCl and protease inhibitor cocktail (Complete; Roche), on ice for 30 minutes. The cell lysate was centrifuged at 15,000 rpm, 4° C. for 30 minutes, and the supernatant was recovered. Western blotting was performed using this cytolysis supernatant. Specifically, 20 µg aliquot of the protein was separated by SDS-PAGE (4-12% polyacrylamide gels), transferred to a PVDF membrane, and incubated with an anti-SOD1 antibody (1:2000 dilution) (Stressgen) or an anti-β-actin antibody (1:5000 dilution) (Sigma-Aldrich). After the incubation, the amount expressed was detected by ECL (Enhanced ChemiLuminescence) using an HRP-linked anti-rabbit IgG antibody (1:5000; GE healthcare) and an HRP-linked anti-mouse IgG antibody (1:5000; GE healthcare). As a result, at all concentrations of sorafenib, a reduction in the expression of SOD1 was observed (FIG. 3D). However, the decreased amount of SOD1 expressed is not attributable to the effectiveness of the drug, since cell death occurred at 30 µM sorafenib.

In Vivo Effect of Sorafenib

Figure 4:
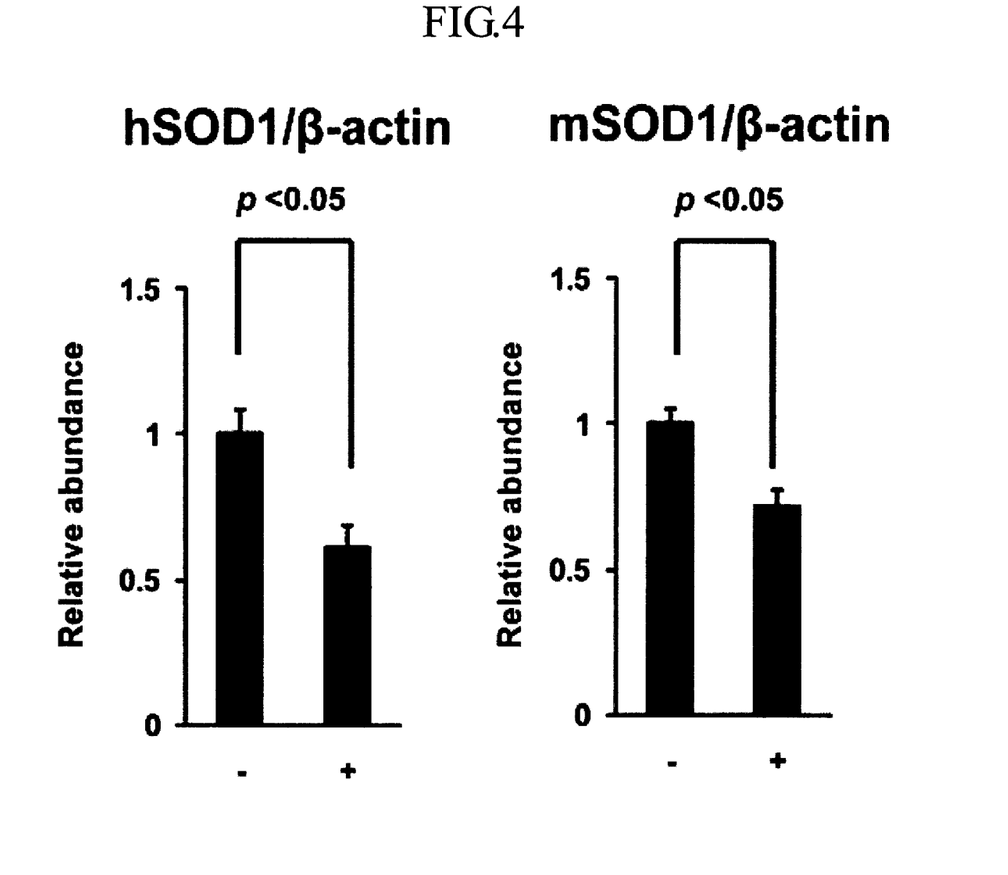
FIG. 4 shows mRNA expression amounts of human SOD1 (hSOD1) and mouse SOD1 (mSOD1) relative to β-actin, in the cells in the spiral cord of SOD1 mutant mouse after administration of sorafenib, wherein "+" shows the expression amount of the sorafenib administration group and "−" shows the expression amount of the control group.

To 8-week-old human SOD1 (G93A) transgenic mice (The Jackson Laboratory) were orally administered sorafenib (60 mg/kg/day) dissolved in 95% ethanol and Cremophol EL or solvent alone as a control, each to 3 mice, 5 days a week for 4 weeks. After administration, the spinal cord was removed. Total RNA was extracted and human and mouse SOD1 mRNA amounts were measured by PCR. As a result, both SOD1 mRNA amounts significantly decreased in the sorafenib administration group (FIG. 4). Judging from these facts, combined with many findings concerning the effects of astrocytes having a mutation in SOD1 on motor neuron damage (Zhong, Z. et al., J. Clin. Invest., 119: 3437-49 (2009)), it is suggested that sorafenib may be useful in preventing or treating ALS.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

This application is based on U.S. provisional patent application No. 61/379,558, the content of which is hereby incorporated by reference.

The invention claimed is:

1. A method of inhibiting the expression of human SOD1 in a cell by administering sorafenib or a pharmaceutically acceptable salt thereof to the cell, wherein the human SOD1 is mutated SOD1.

2. The method of claim 1, wherein sorafenib is administered.

3. The method of claim 1, wherein sorafenib tosylate is administered.

4. The method of claim 1, wherein the cell is in a subject suffering from amyotrophic lateral sclerosis (ALS) accompanied by a mutation in SOD1.

5. The method of claim 4, wherein sorafenib is administered.

6. The method of claim 4, wherein sorafenib tosylate is administered.

* * * * *